US010667366B2

(12) United States Patent
Pereyra et al.

(10) Patent No.: US 10,667,366 B2
(45) Date of Patent: May 26, 2020

(54) LIGHTING DEVICES WITH AUTOMATIC LIGHTING ADJUSTMENT

(71) Applicants: Rodrigo M. Pereyra, Salem, MA (US); Joseph A. Olsen, Gloucester, MA (US); Alan Sarkisian, Marblehead, MA (US); Siddhant Sharma, Brighton, MA (US)

(72) Inventors: Rodrigo M. Pereyra, Salem, MA (US); Joseph A. Olsen, Gloucester, MA (US); Alan Sarkisian, Marblehead, MA (US); Siddhant Sharma, Brighton, MA (US)

(73) Assignee: OSRAM SYLVANIA Inc., Wilmington, MA (US)

( * ) Notice: Subject to any disclaimer, the term of this patent is extended or adjusted under 35 U.S.C. 154(b) by 0 days.

(21) Appl. No.: 16/023,516

(22) Filed: Jun. 29, 2018

(65) Prior Publication Data

US 2020/0008282 A1    Jan. 2, 2020

(51) Int. Cl.
*H05B 37/02*    (2006.01)
*G06T 7/00*    (2017.01)
*H05B 47/105*    (2020.01)
*A61B 90/30*    (2016.01)
*G06T 7/73*    (2017.01)
*G06T 7/50*    (2017.01)
*A61B 5/16*    (2006.01)

(52) U.S. Cl.
CPC .......... *H05B 47/105* (2020.01); *A61B 5/163* (2017.08); *A61B 90/30* (2016.02); *G06T 7/0016* (2013.01); *G06T 7/50* (2017.01); *G06T 7/74* (2017.01)

(58) Field of Classification Search
None
See application file for complete search history.

(56) References Cited

U.S. PATENT DOCUMENTS

| 2007/0258243 | A1 | 11/2007 | Segall | |
| 2014/0039273 | A1 | 2/2014 | Kim et al. | |
| 2015/0257735 | A1* | 9/2015 | Ball | A61B 8/5261 |
| | | | | 600/440 |
| 2017/0099479 | A1* | 4/2017 | Browd | G06F 3/011 |
| 2018/0180890 | A1* | 6/2018 | Baerenrodt | G02B 3/14 |

FOREIGN PATENT DOCUMENTS

EP    1134491 A2    9/2001

OTHER PUBLICATIONS

Morrish, Ian, International Search Report and Written Opinion of the International Searching Authority, for counterpart application PCT/US2019/038125, dated Oct. 22, 2019, European Patent Office, Rijswijk, The Netherlands, 14 pages.

* cited by examiner

*Primary Examiner* — Minh D A
(74) *Attorney, Agent, or Firm* — Yutian Ling (57) ABSTRACT

Lighting systems and associated controls that can provide active control of lighting device settings, such as on/off, color, intensity, focal length, beam location, beam size and beam shape. In some examples, lighting systems may include eye tracking technology and sensor feedback for one or more lighting device settings and may be configured with depth perception and cavity or incision recognition capability through image or video processing.

16 Claims, 9 Drawing Sheets

LIGHTING DEVICES WITH AUTOMATIC LIGHTING ADJUSTMENT

FIELD OF THE DISCLOSURE

The present disclosure generally relates to the field of lighting devices. In particular, the present disclosure is directed to lighting devices with automatic lighting adjustment.

BACKGROUND

Task lighting provides increased illuminance for a particular activity. A task light can be configured to be wearable, such as configured to be mountable to a person's head or torso, or not, such as an overhead or work-surface mounted light. Task lighting can be useful in any of a variety of activities, such as activities where increased illumination of small or recessed areas is desired, such as activities performed by jewelers, gemologists, watchmakers, photographers, dentists, geologists, microelectronics designers or technicians, tattoo artists, and surgeons, etc.

In the surgical field, surgical headlamps are one of the principal sources of illumination in an operating room (OR). Surgeons rely on surgical headlamps as a secondary source when the overhead lamps are blocked (shadowing) or in deep cavity surgeries where additional lighting is needed for visual acuity (e.g. cardiovascular, thyroid, orthopedic surgery etc.). Headlamps have the advantage of being in line with the surgeon's field of view, delivering light in the general area where the surgeon is seeing.

Despite their ubiquitous use in the OR, current headlamps have significant limitations particularly in the area of controls. A typical process of adjusting and controlling a headlamp includes, prior to surgery, doing an initial setup of the headlamp (position, intensity, beam size, focus etc.), which can be tailored to a particular surgical procedure. Due to sterility concerns and because a surgeon's hands are occupied during a surgery, this is typically the only time the surgeon can make lighting adjustments. If a change is required, e.g., after surgery begins, another person may need to make the adjustment. If the surgeon wishes to make the adjustment, e.g., by hand, the control features must be sterilized components because if the surgeon were to come in contact with a component of the headlamp that isn't sterilized, he would need to stop surgery in order to re-sterilize before proceeding.

SUMMARY OF THE DISCLOSURE

In one implementation, the present disclosure is directed to a method of controlling a lighting device. The method includes receiving, at a processor, position sensor data, the position sensor data representing a position of at least one of a user's head and a user's eyes, determining, by the processor, whether the user is looking at a task area based on the position sensor data, and controlling, by the processor, an intensity of light emitted by the lighting device or turning the light on or off in response to determining whether the user is looking at the task area.

In some embodiments, the position sensor data is head position sensor data indicating a position of a user's head, and determining whether the user is looking at the task area includes calculating, by the processor, an angle of the user's head from the head position sensor data, and determining, by the processor, whether the calculated angle is within a first range of angles associated with the user looking at the task area. In some embodiments, the position sensor data is eye position sensor data indicating a position of a user's eyes, and determining whether the user is looking at the task area includes determining, by the processor, whether the eye position sensor data is within a first range of positions associated with the user looking at the task area. In some embodiments, the first range of positions are associated with the user looking through loupes. In some embodiments, the method further includes determining, by the processor, a location where the user is looking based on the eye position sensor data, and controlling, by the processor, a location of a beam of light emitted by the lighting device to be substantially coincident with the location where the user is looking. In some embodiments, the eye position sensor data is collected by an eye position sensor, and the method further includes pointing the lighting device at a first one of a plurality of targets, recording sensor data from the eye position sensor while a user is looking at the first one of the plurality of targets, and determining a set of calibrating parameters for translating a coordinate of the sensor data to a lighting device coordinate. In some embodiments, the set of calibration parameters are parameters of a two-dimensional linear approximation. In some embodiments, the set of calibration parameters represent a translation and a rotation of a coordinate system of the eye position sensor to a coordinate system of the lighting device.

In another implementation, the present disclosure includes a lighting system. The lighting system includes a lighting device, a position sensor, and a processor coupled to the lighting device and position sensor configured to receive position sensor data from the position sensor, the position sensor data representing a position of at least one of a user's head and a user's eyes, determine whether the user is looking at a task area based on the position sensor data, and control an intensity of light emitted by the lighting device or turn the light on or off in response to determining whether the user is looking at the task area.

In some embodiments, the position sensor is a head position sensor, the position sensor data indicates a position of a user's head, and the processor is further configured to calculate an angle of the user's head from the position sensor data, and determine whether the calculated angle is within a first range of angles associated with the user looking at the task area. In some embodiments, the position sensor is an eye position sensor, the position sensor data indicates a position of a user's eyes, and the processor is further configured to determine whether the position sensor data is within a first range of positions associated with the user looking at the task area. In some embodiments, the first range of positions are associated with the user looking through loupes. In some embodiments, the processor is further configured to determine a location where the user is looking based on the position sensor data, and control a location of a beam of light emitted by the lighting device to be substantially coincident with the location where the user is looking. In some embodiments, the processor is further configured to point the lighting device at a first one of a plurality of targets, record sensor data from the eye position sensor while a user is looking at the first one of the plurality of targets, and determine a set of calibrating parameters for translating a coordinate of the sensor data to a lighting device coordinate. In some embodiments, the set of calibration parameters are parameters of a two-dimensional linear approximation. In some embodiments, the set of calibration parameters represent a translation and a rotation of a coordinate system of the eye position sensor to a coordinate system of the lighting device.

In another implementation, the present disclosure includes a method of controlling a surgical lighting device. The method includes capturing, by an image capture device, an image of a surgery field, detecting, with a processor, an incision in the image, determining, with the processor, at least one property of the incision, and adjusting, by the processor, at least one setting of the surgical lighting device to illuminate the incision based on the at least one property of the incision.

In some embodiments, the at least one property of the incision includes at least one of a size, shape, and depth of the incision. In some embodiments, determining at least one property of the incision includes determining a size of the incision, and adjusting at least one setting of the surgical lighting device includes adjusting a beam size according to the determined size of the incision. In some embodiments, determining at least one property of the incision includes determining a shape of the incision, and adjusting at least one setting of the surgical lighting device includes adjusting a beam shape according to the determined shape of the incision. In some embodiments, determining at least one property of the incision includes determining a depth of the incision, and adjusting at least one setting of the surgical lighting device includes adjusting a beam focal length or intensity according to the determined depth of the incision. In some embodiments, the method further includes matching, by the processor, the detected incision with a first incision in a plurality of incisions stored in an incision database, the incision database associating each of the plurality of incisions with a predefined surgical lighting device setting, in which adjusting at least one setting of the surgical lighting device includes adjusting the at least one setting to correspond to the predefined surgical lighting device setting associated with the first incision.

In another implementation, the present disclosure includes a lighting system. The lighting system includes an image capture device configured to capture an image of a surgery field, a surgical lighting device, and a processor coupled to the image capture device and the surgical lighting device configured to detect an incision in the image, determine at least one property of the incision, and adjust at least one setting of the surgical lighting device to illuminate the incision based on the at least one property of the incision.

In some embodiments, the at least one property of the incision includes at least one of a size, shape, and depth of the incision. In some embodiments, the at least one property of the incisions includes a size of the incision and the processor is further configured to adjust a beam size of a light beam emitted by the surgical lighting device according to the determined size of the incision. In some embodiments, the at least one property of the incisions includes a shape of the incision and the processor is further configured to adjust a beam shape of a light beam emitted by the surgical lighting device according to the determined shape of the incision. In some embodiments, the at least one property of the incisions includes a depth of the incision and the processor is further configured to adjust a beam focal length or intensity of a light beam emitted by the surgical lighting device according to the determined depth of the incision. In some embodiments, the processor is further configured to match the detected incision with a first incision in a plurality of incisions stored in an incision database, the incision database associating each of the plurality of incisions with a predefined surgical lighting device setting, in which the processor is configured to adjust at least one setting of the surgical lighting device by adjusting the at least one setting to correspond to the predefined surgical lighting device setting associated with the first incision.

BRIEF DESCRIPTION OF THE DRAWINGS

For the purpose of illustrating the disclosure, the drawings show aspects of one or more embodiments of the disclosure. However, it should be understood that the present disclosure is not limited to the precise arrangements and instrumentalities shown in the drawings, in which.

DETAILED DESCRIPTION

Aspects of the present disclosure include lighting systems and associated controls that can provide active control of lighting device settings, such as on/off, color, intensity, focal length, beam location, beam size and beam shape. In some examples, control systems can provide lighting system control in a sterile manner, which can be advantageous for surgical lighting applications. In some examples, lighting systems may include eye tracking technology and sensor feedback for one or more lighting device settings and may be configured with depth perception and cavity or incision recognition capability through image or video processing. Surgical lighting systems of the present disclosure may also include surgical lighting presets, in which a lighting device such as a surgical headlamp can be tailored and optimized for particular surgeries. For example, beam size, beam shape, focal length, intensity, etc., may be preset ahead of time, reducing a surgeon's setup time in the operating room. Aspects of the present disclosure also include machine learning algorithms configured to optimize one or more lighting device settings, for example, based on a user's movements, head position, duration of use, etc. Aspects of the present disclosure also include calibration procedures for calibrating an eye position sensor with an adjustable lighting device for a particular user.

Intelligent lighting devices with automatic lighting adjustment made in accordance with the present disclosure may be used in surgical theaters to improve sterility in a surgical environment and provide a sterile means of control and automation of surgical lighting, which can have a positive influence on a surgeon's ability to perform his or her tasks. Lighting devices disclosed herein can help reduce the dependence of a surgeon on other people within the operating room to make changes to surgical lighting device settings. Benefits may also include glare reduction in the surgical field and operating room. Surgical rooms typically include a large number of metallic items that cause specular reflections and unwanted glare. By tailoring the settings of surgical lighting and enabling improved lighting control during surgery, glare can be reduced and surgical performance improved. For example, incision size can be reduced and tissue trauma can also be reduced from pulling occluding tissue out of the way. These improvements can directly lead to improved clinical outcomes, as reducing incision size and tissue trauma may result in mitigating tissue trauma and potentially shortening recovery times.

Figure 1:
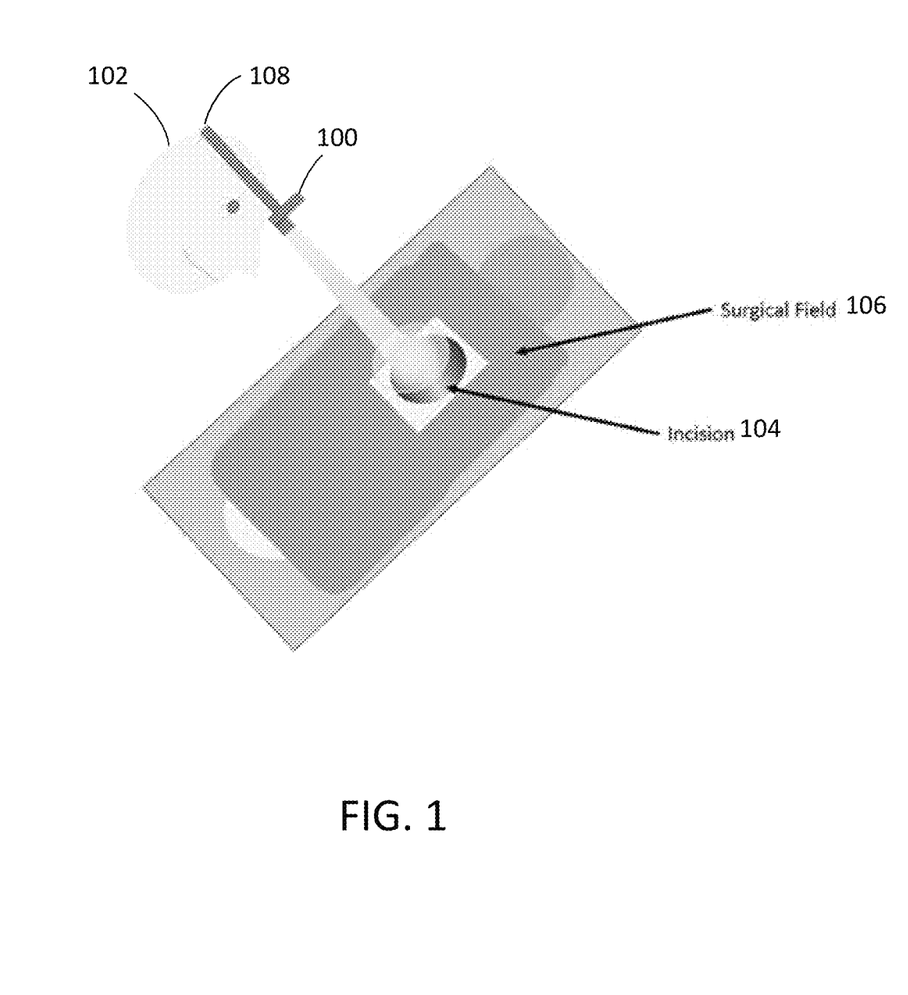
FIG. 1 is a perspective view of a surgical lighting device system in use.

FIG. 1 shows one example environment where intelligent lighting devices with automatic lighting adjustment of the present disclosure may be used, namely, surgical applications. FIG. 1 illustrates an example surgical lighting device 100 in the form of a surgical headlamp for use by a surgeon 102 to provide increased illumination of an incision 104 within a surgical field 106. As discussed more fully below, lighting device 100 can be operably coupled to a variety of sensors and at least one computing device that is configured to provide automated control of one or more settings of lighting device 100.

Figure 2:
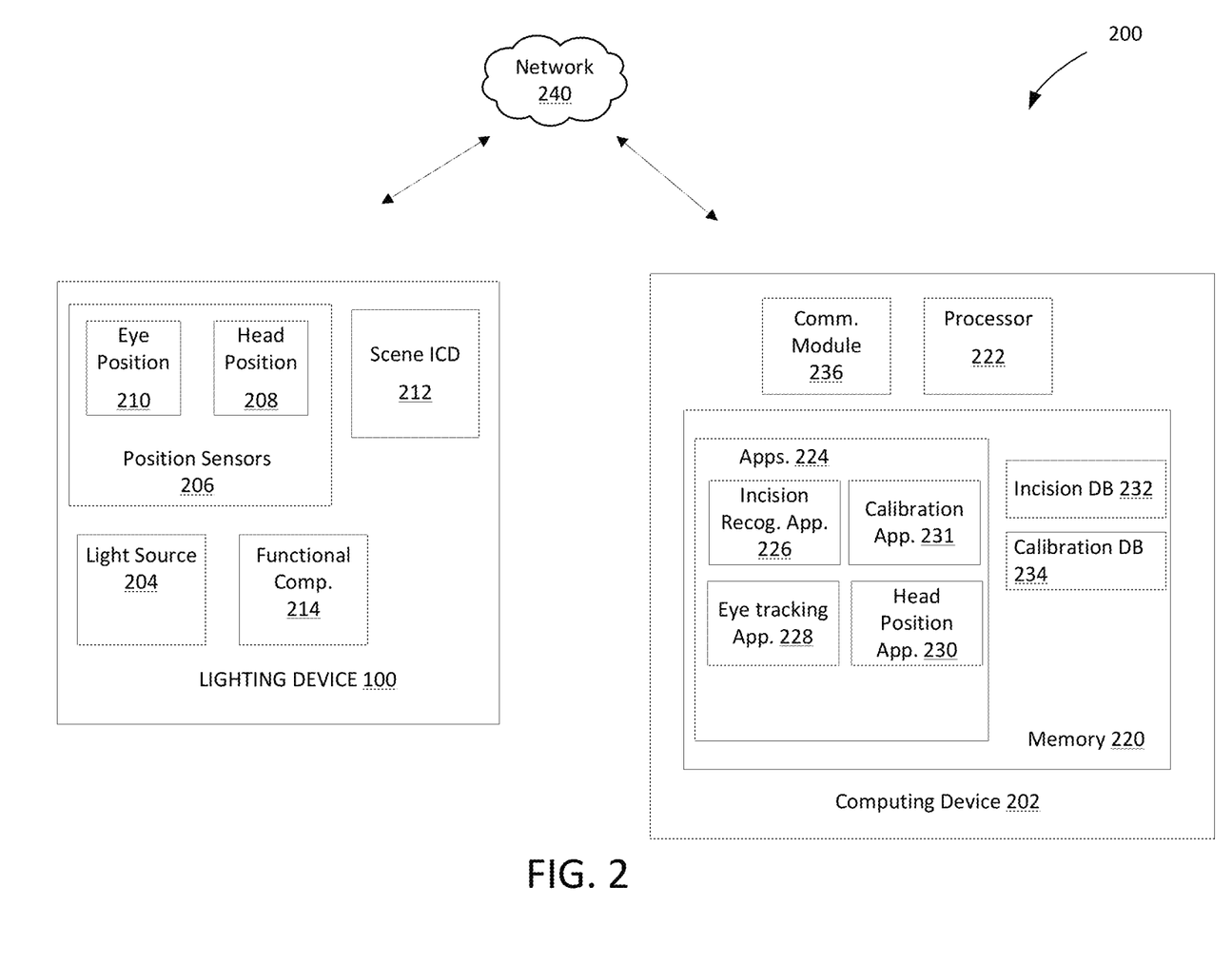
FIG. 2 is a functional block diagram of the system of FIG. 1.

FIG. 2 is a functional block diagram of a lighting system 200 that includes lighting device 100 communicatively coupled to a computing device 202 configured to determine one or more settings of the lighting device. Although FIG. 2 is discussed in connection with surgical lighting device 100 of FIG. 1, as will be appreciated by a person having ordinary skill in the art, the teachings of the present disclosure may be applied to other task lighting systems, including overhead surgical lighting and task lighting for non-surgical applications. In the illustrated embodiment, lighting device 100 may include one or more light sources 204. Light source 204 may be any semiconductor light source device, such as, for example, a light-emitting diode (LED), an organic light-emitting diode (OLED), a polymer light-emitting diode (PLED), or a combination thereof, among others. A given solid-state emitter may be configured to emit electromagnetic radiation (e.g., light), for example, from the visible spectral band, the infrared (IR) spectral band, the ultraviolet (UV) spectral band, or a combination thereof, among others. In some embodiments, a given solid-state emitter may be configured for emissions of a single correlated color temperature (CCT) (e.g., a white light-emitting semiconductor light source). In some other embodiments, a given solid-state emitter may be configured for color-tunable emissions; for instance, a given solid-state emitter may be a multi-color (e.g., bi-color, tri-color, etc.) semiconductor light source configured for a combination of emissions, such as red-green-blue (RGB), red-green-blue-yellow (RGBY), red-green-blue-white (RGBW), dual-white, or a combination thereof, among others. In some cases, a given solid-state emitter may be configured, for example, as a high-brightness semiconductor light source. In other examples, light source 204 may be an external light source powered by battery or mains power and coupled to a headlamp via, e.g., a fiber optic bundle.

In some examples, settings of lighting device 100 that are controllable by computing device 202 include at least one of on/off, color, intensity, focal length, beam location, beam size and beam shape. Control of beam focal length, location, size, and shape can allow for tailoring the light generated by lighting device 100 to a particular task. For example, for surgical lighting, beam shape, size, and focal length can be tailored to a particular incision size and depth such that the areas of the body below the surface of a patient's skin that are being operated on are sufficiently illuminated and unnecessary lighting of objects adjacent the incision, such as other portions of surgical field 106 and surgical objects, is avoided. Any of a variety of systems for adjusting one or more of beam focal length, location, size, and shape may be used. For example, spatial adjustment of the position and size of a beam of light emitted by lighting device 100 can be accomplished through mechanical adjustors, such as actuators, microelectromechanical systems (MEMs) or through the design of the light engine itself. Examples include the lighting systems described in U.S. Pat. No. 9,332,619, titled "Solid-State Luminaire With Modular Light Sources And Electronically Adjustable Light Beam Distribution," and U.S. Pat. No. 9,801,260, titled, "Techniques And Graphical User Interface For Controlling Solid-State Luminaire With Electronically Adjustable Light Beam Distribution," each of which is incorporated by reference herein in its entirety. Commercially-available lighting devices that include beam adjustment capability that may be applied to lighting devices made in accordance with the present disclosure include micro-structured Adaptive Front-lighting System (uAFS) devices and OMNIPOINT™ array-based LED lighting devices, available from OSRAM, Munich, Germany.

Lighting device 100 may also include one or more position sensors 206 for generating position signals for use in the control of one or more settings of the lighting device. Position sensors 206 may include a head position sensor 208, such as an accelerometer or gyroscope, that is coupled to a user's head and that can be used to determine a position of the user's head. Position sensors 206 may also include an eye position sensor 210 that, as described more below, may be used to determine a location where the user is looking so that a location of a light beam generated by lighting device 100 may be substantially coincident with the location the user is looking.

Lighting device 100 may also include at least one scene image capture device (ICD) 212 that, as described herein, can be used to capture an image of the scene being viewed by the user and that is being illuminated by the lighting device for adjusting one or more lighting device settings. Scene ICD 212 may be programmed or otherwise configured to capture or acquire images of an area such as surgical field 106 (FIG. 1). For example, Scene ICD 212 may have a field of view (FOV) that covers substantially all of an illumination area of light sources 204. In some embodiments, the FOV of scene ICD 212 may be larger than the illumination area, which may help ensure the captured image has sufficient size to fully include the area of interest. Scene ICD 212 may be any device configured to capture digital images, such as a still camera (e.g., a camera configured to capture still photographs) or a video camera (e.g., a camera configured to capture moving images including a plurality of frames), and may be integrated, in part or in whole, with lighting device 100 or a separate device that is distinct from the lighting device 100. The images can be permanently (e.g., using non-volatile memory) or temporarily stored (e.g., using volatile memory), depending on a given application, so that they can be analyzed by computing device 202, as further described herein. In an example embodiment, scene ICD 212 is a single or high resolution (megapixel) camera that captures and processes real-time video images of an illumination area of lighting device 100. Scene ICD 212 may be configured, for example, to acquire image data in a periodic, continuous, or on-demand manner, or a combination thereof, depending on a given application. In accordance with some embodiments, scene ICD 212 can be configured to operate using light, for example, in the visible spectrum, the infrared (IR) spectrum, or the ultraviolet (UV) spectrum, among others. Componentry of scene ICD 212 (e.g., optics assembly, image sensor, image/video encoder) may be implemented in hardware, software, firmware, or a combination thereof.

Lighting device 100 may also include any of a variety of additional functional components 214 known in the art. For example, if light source 204 is an external light source, additional functional components 214 may include a fiber optic bundle for transmitting light from the external light source to a light emitting portion of the lighting device 100. Functional components 214 may also include an optical system including a variable diaphragm and a lens for adjusting beam size and shape. In other examples, if light source 204 includes one or more solid state light sources located in a headlamp, additional functional components 214 may include a modular power source, such as a waist mounted battery.

In accordance with some embodiments, computing device 202 may include a memory 220. Memory 220 can be of any suitable type (e.g., RAM and/or ROM, or other suitable memory) and size, and in some cases may be implemented with volatile memory, non-volatile memory, or a combination thereof. Memory 220 may be utilized, for example, for processor workspace and/or to store media, programs, applications, content, etc., on a temporary or permanent basis. Also, memory 220 can include one or more modules stored therein that can be accessed and executed, for example, by processor(s) 222.

Memory 220 also may include one or more applications 224 stored therein. For example, in some cases, memory 220 may include or otherwise have access to an image/video recording application or other software that permits image capturing/video recording using scene ICD 212, as described herein. In some cases, memory 220 may include or otherwise have access to an image/video playback application or other software that permits playback/viewing of images/video captured using scene ICD 212. In some embodiments, one or more applications 224 may be included to facilitate presentation and/or operation of graphical user interfaces (UIs) such as incision light setting UI 700 described herein. Applications 224 may include an incision recognition application 226 for recognizing an incision and/or determining a sized and/or depth of an illumination area detected in images captured by scene ICD 212, an eye tracking application 228 for receiving position data generated by eye position sensor 210 and determining a position of a user's eye and a location where a user is looking, a head position application 230 for determining a position of a user's head, and a calibration application 231 for performing a calibration procedure for calibrating lighting device 100. Memory 220 may also include one or more databases, such as an incision database 232 for storing information on the characteristics of a plurality of different types of incisions and a calibration database 234 for storing calibration parameters determined during a calibration procedure performed with calibration application 203. Computing device 202 may also be programmed with one or more machine learning algorithms for continuously or periodically adjusting the values of calibration parameters stored in calibration database 234, for example, based on particular user characteristics.

Computing device 202 may also include a communication module 236, in accordance with some embodiments. Communication module 236 may be configured, for example, to aid in communicatively coupling computing device 202 with one or more components of lighting device 100. Communication module 236 can be configured, for example, to execute any suitable wireless communication protocol that allows for data/information to be passed wirelessly. Computing device 202 and one or more components of lighting device 100 can each be associated with a unique ID (e.g., IP address, MAC address, cell number, or other such identifier) that can be used to assist the communicative coupling therebetween. Some example suitable wireless communication methods that can be implemented by communication module 236 may include: radio frequency (RF) communications (e.g., Wi-Fi®; Bluetooth®; near field communication or NFC); IEEE 802.11 wireless local area network (WLAN) communications; infrared (IR) communications; cellular data service communications; satellite Internet access communications; custom/proprietary communication protocol; and/or a combination of any one or more thereof. In some embodiments, computing device 202 may be capable of utilizing multiple methods of wireless communication. In some such cases, the multiple wireless communication techniques may be permitted to overlap in function/operation, while in some other cases they may be exclusive of one another. In some cases a wired connection (e.g., USB, Ethernet, FireWire, or other suitable wired interfacing) may also or alternatively be provided between computing device 202 and the other components of system 200.

In some instances, computing device 202 may be configured to be directly communicatively coupled with lighting device 100. In some other cases, however, computing device 202 and lighting device 100 optionally may be indirectly communicatively coupled with one another, for example, by an intervening or otherwise intermediate network 240 for facilitating the transfer of data between the computing device 202 and building system components. Network 240 may be any suitable communications network, and in some example cases may be a public and/or private network, such as a private local area network (LAN) operatively coupled to a wide area network (WAN) such as the Internet. In some instances, network 240 may include a wireless local area network (WLAN) (e.g., Wi-Fi® wireless data communication technologies). In some instances, network 240 may include Bluetooth® wireless data communication technologies. In some cases, network 240 may include supporting infrastructure and/or functionalities such as a server and a service provider, but such features are not necessary to carry out communication via network 240.

Position Sensors

As noted above, lighting device 100 may include a head position sensor 208 and an eye position sensor 210. Head position sensor 208 can be configured to generate a position signal according to a position of a user's head, which can be used by head position application 230 executed by, e.g., computing device 202 or a separate processor (e.g., an application specific, dedicated, or embedded microprocessor) for controlling one or more settings of lighting device 100 according to a position of the user's head. For example, in the case of example surgical lighting device 100 which is a surgical headlamp, head position sensor 208 can be coupled to the headlamp for determining a position of the user's head. Lighting device 100 may be configured to turn on and/or have a first intensity when the user's head is in a first position or range of positions associated with looking at a task area, such as surgical field 106 (FIG. 1) and turn off or dim to a lower intensity when the user's head is not in the first position or within the first range of positions, such as when the user looks up from the surgical field. Such a feature can be beneficial to avoid unnecessarily blinding others in the operating room with lighting device 100 when the surgeon looks up and for conserving battery power. The first position or range of positions for turning lighting device 100 on can be set based on a surgeon's preference or the particular operation being performed. In the case of surgical lighting device 100, on positions would often be positions associated with the surgeon looking down, but could be set to other positions, e.g., for operations performed at eye level. As will be appreciated, head position sensor 208 may also be used in connection with overhead lights for turning on and off or adjusting the intensity of overhead task lights when the user looks towards or away from a task area. Whether the lighting device is an overhead task light or headlamp, head position sensor 208 may be directly coupled to a user's head such that the head position sensor moves with the user's head. In other examples, head position sensor 208 may not be physically coupled to the user's head and may use any positioning sensor known in the art to determine a position of the user's head, such as through the use of infrared light, radio waves, or acoustic waves to determine a position of the surgeon's head.

Figure 3:
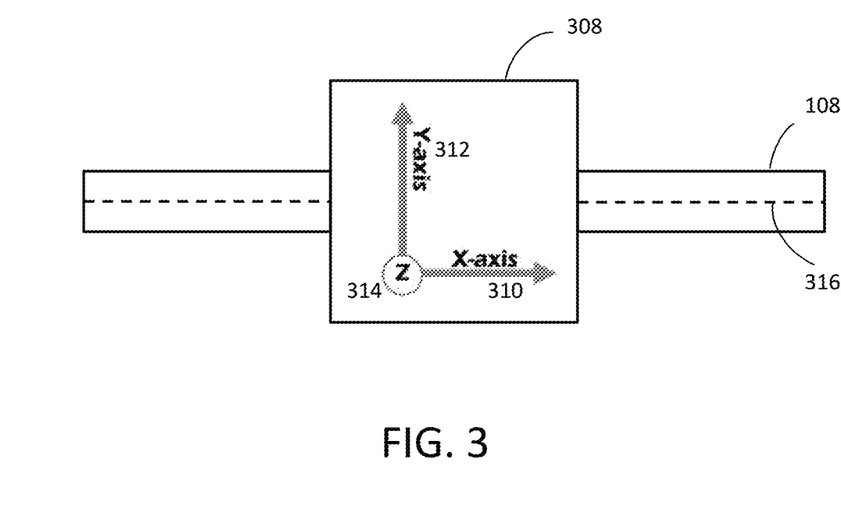
FIG. 3 is illustrates a head position sensor coupled to a circumferential headband.

FIG. 3 illustrates one example of a head position sensor 308 coupled to a circumferential headband 108 (see also FIG. 1) to be worn by a user to monitor a position of the user's head. Head position sensor 308 has three axes—x axis 310, y axis 312 and z axis 314. A first range of positions defined as some reference points (x, y, z), and a range (+/−Δx, +/−Δy, +/−Δz) can be used to define when the lighting device is on. In one example, when any one of the x, y, or z values being output by head position sensor 308 exceeds the first range of positions (x+/−Δx, y+/−Δy, z+/−Δz), the intensity of the lighting device may be reduced or the lighting device turned off. In the illustrated example, head position sensor 308 includes an accelerometer, which is configured to characterize a lateral force of movement when the head position sensor 308 is physically moved, and the force of gravity that the head position sensor experiences when in a stationary position. In one example, the force of gravity component of the position signals generated by head position sensor 308 may be used to control whether lighting device 100 is on or off or dimmed. In one example, the force of gravity is expressed by a 3-axes representation, into each axial component $x_g$, $y_g$, $z_g$ such that $\sqrt{x_g^2+y_g^2+z_g^2}=g$, where g is the constant force of gravity.

As shown in FIG. 3, head position sensor 308 can be attached to circumferential headband 108 and oriented relative to the circumferential headband such that x axis 310 is substantially parallel to a longitudinal axis 316 of the circumferential headband. In such an example, x axis 310 will be substantially horizontal, e.g., substantially parallel to the ground when the user is standing upright and looking straight ahead. Y axis 312 may be substantially perpendicular to a plane extending through longitudinal axis 316 such that, in use, the y axis is substantially vertical when the user is standing upright and looking forward. With head position sensor 308 oriented relative to circumferential headband 108 as shown in FIG. 3, a first position or range of positions of head position sensor 308 for turning lighting device 100 on can be defined as a first value or range of values of the $x_g$, $y_g$ components, and/or the corresponding angle calculated as the inverse tangent of those components. In one example, when the user will be looking down to perform a task, a first range of values of the inverse tangent of $$\frac{x_g}{y_g}$$

for turning lighting device 100 on may be in the range of approximately −16 degrees to approximately −90 degrees, and lighting device 100 may be configured to turn off or dim when the inverse tangent is between approximately −16 degrees and approximately 45 degrees. Head position application 230 may be configured to receive position signals generated by head position sensor 208, calculate a position of the user's head according to the position signals, and automatically adjust the intensity of light output by light source 204 between a first intensity when the user's head is in a first position or range of positions and a second intensity when the user's head is not in the first range of positions.

Figure 4A:
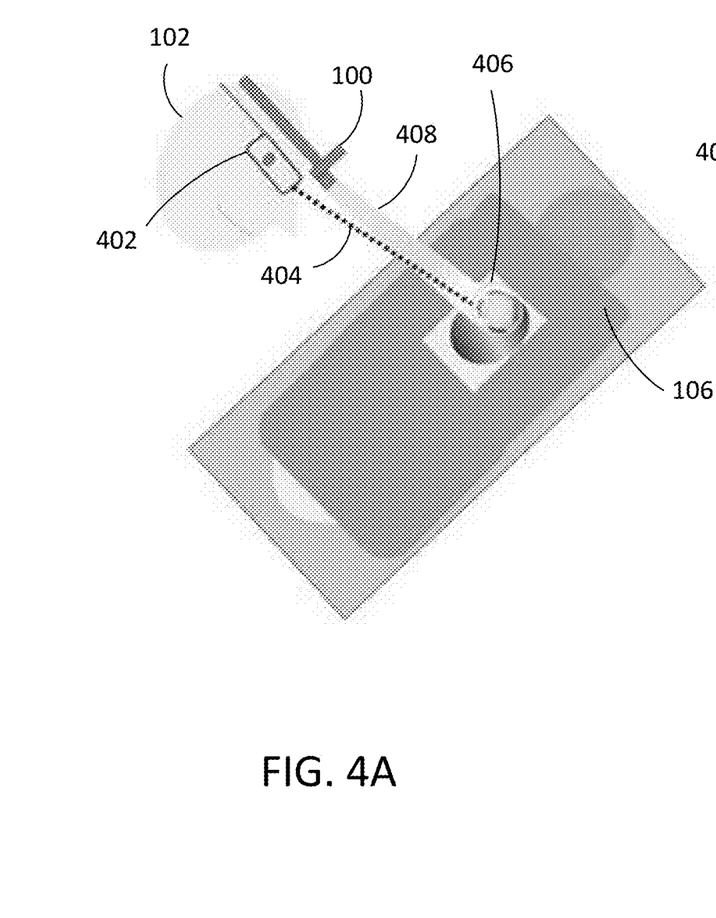
FIG. 4A is a perspective view of a surgical headlamp with eye tracking and spatial beam control in use, showing a surgeon looking at a first location.
Figure 4B:
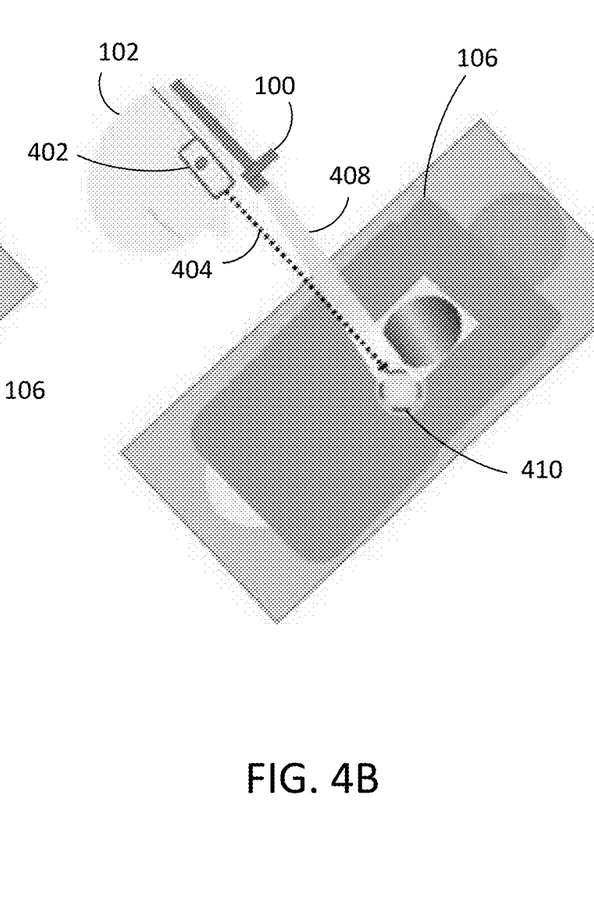
FIG. 4B is a perspective view of the surgical headlamp in use of FIG. 4A, showing the surgeon looking at a second location and the surgical headlamp automatically adjusting the beam location to be substantially coincident with the second location.

Position sensors 206 can also include an eye position sensor 210 for determining a position of a user's eye. As noted above, the location of a light beam generated by lighting device 100 may be controllable, for example, by computing device 202. By combining eye position sensor 210 with spatial beam control, lighting device can be configured to automatically move a position of a light beam to be substantially coincident with a location where the user is looking. For example, FIGS. 4A and 4B illustrate lighting device 100 being used by surgeon 102 and also show an embodiment of an eye position sensor 402 incorporated into glasses for tracking the position of the surgeon's eyes. FIG. 4A includes dotted line 404 illustrating a first location 406 in surgical field 106 where the surgeon is looking. Eye tracking application 228 can receive position information generated by eye position sensor 402 and determine the position of first location 406, which can be used to control a location of beam 408 so that the beam location is substantially coincident with the first location 406. In FIG. 4B, surgeon 102 has adjusted his gaze to look at a second location 410. Eye position sensor 402 can detect the movement of the surgeon's eyes and communicate the position information to computing device 202 for determining second location 410 and adjusting a position of beam 408 to be substantially coincident with the second location.

Eye position sensor 210 may also be used to control other settings of lighting device 100. For example, lighting device 100 may be configured to turn off or dim when the user looks away from a task area. Eye position sensor 210 may generate eye position data and eye tracking application 228 may be programmed with a first range of eye positions associated with turning lighting device on or emitting a first intensity of light, and the eye tracking application may be configured to dim or turn off the lighting device when the eye position data is outside of the first range of positions. In one example, where the user uses loupes (not illustrated) to magnify a task area, eye tracking application 228 may be configured to turn lighting device on when data from eye position sensor 210 indicates the user is looking through the loupes and turn off or dim the light when the data from eye position sensor indicates the user is not looking through the loupes.

Figure 5:
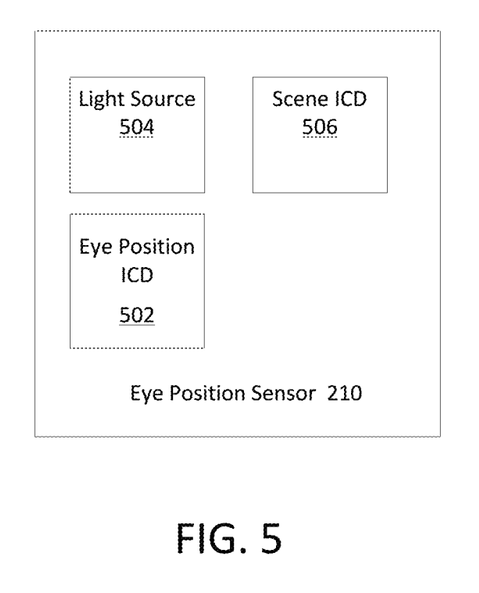
FIG. 5 is a functional block diagram of an eye position sensor.

Any of a variety of eye position sensors known in the art may be used for eye position sensor 210. FIG. 5 is a functional block diagram of one example of eye position sensor 210 and includes at least one eye position image capture device (ICD) 502 that records video or still images of a user's eye. In some examples, eye position sensor 210 may also include a light source 504, such as an infrared or near-infrared light source, for creating reflections in the user's eyes that can be captured by eye position ICD 502 to facilitate determining when a change in a position of the user's eye occurs. In some examples, eye position sensor 210 may also include a scene ICD 506 for capturing an image of the scene the user is looking at, which can be used to generate a plot that illustrates a location within the scene the user is looking. In other examples, eye position sensor 210 may not have a separate scene ICD and may instead utilize images captured by scene ICD 212 (FIG. 2). As shown in FIGS. 4A and 4B, in one example, eye position sensor 210 may be embodied in glasses or another structure coupled to a user's face. In other examples, at least eye position ICD 502 and light source 504 may be located in another location, e.g., a fixed location. One example of a commercially available eye position sensor that may be used is the Tobii Pro Glasses 2 available from Tobii AB (https://www.tobiipro.com/).

Video/Image Processing for Beam Control and Light Intensity

Figure 6A:
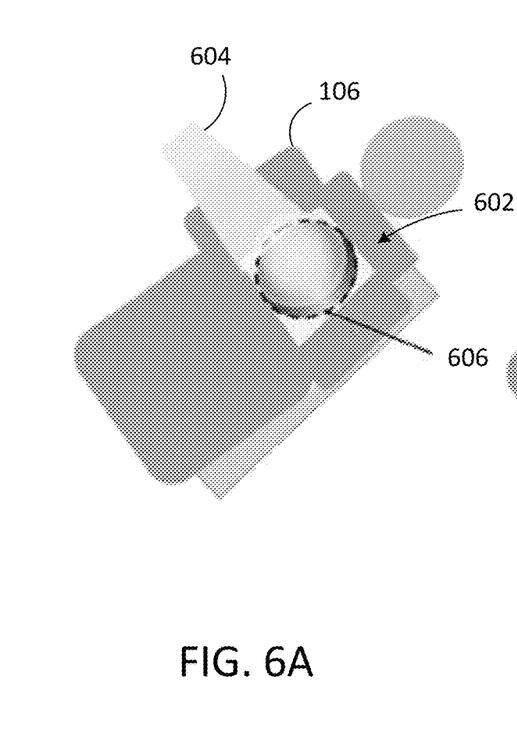
FIG. 6A shows a first incision in surgical field illuminated by light beam having a first size and shape for illuminating the first incision.
Figure 6B:
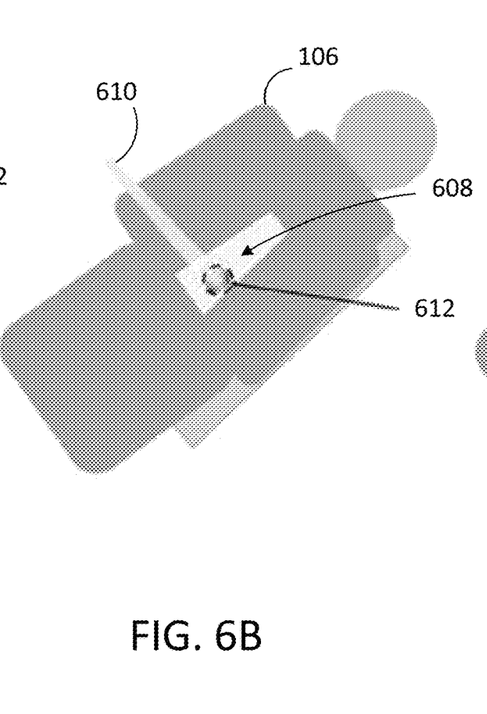
FIG. 6B shows a second incision in surgical field illuminated by light beam having a second size and shape for illuminating the second incision.
Figure 6C:
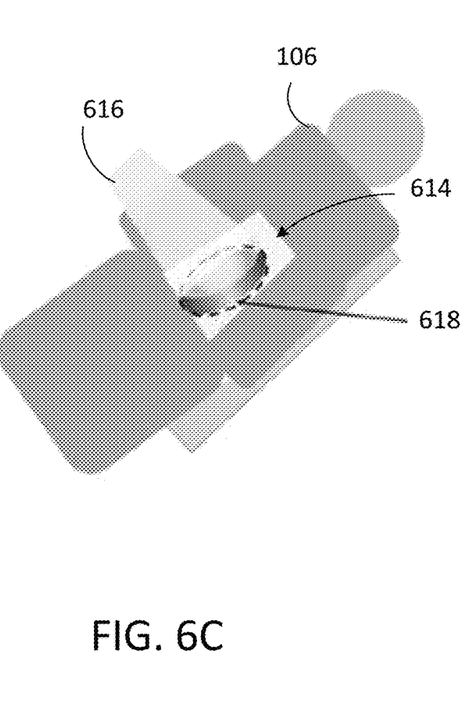
FIG. 6C shows a third incision in surgical field illuminated by light beam having a third size and shape for illuminating the third incision.

Computing device 202 may be configured with image recognition applications for automatically adjusting one or more settings of lighting device 100. For example, optimal lighting device settings may vary with a task, such as the size and depth of an area where increased illumination from lighting device 100 is desired. In the case of surgical lighting, the size and depth of incisions can vary depending on the surgery. Incisions may be as small as a 1" in diameter (e.g. neo-natal orthopedic surgery) and range to ~8" to 10" or more, e.g., thoracic open heart surgery. Lighting device 100 can be configured to automatically adjust one or more settings, such as color, intensity, focal length, beam size and beam shape to optimally illuminate an incision. FIGS. 6A, 6B, and 6C illustrate one example of adjusting light beam characteristics according to incision size, shape, and depth. FIG. 6A shows a first incision 602 in surgical field 106 illuminated by light beam 604, where optimal settings for the light beam include a generally circular beam shape and a beam size that is approximately equal to a diameter of an outer perimeter 606 of the incision. FIG. 6B shows a smaller incision 608. Optimum settings for the light beam 610 include a generally circular beam shape and a beam size that is approximately equal to a diameter of an outer perimeter 612 of the incision. FIG. 6C shows a third incision 614. Optimum settings for the light beam 616 include a generally oval or elliptical shape and a beam size that is approximately equal to a size of an outer perimeter 618 of the incision. In addition to beam size and shape, beam intensity and focal length may also be adjusted according to a depth of the incision.

Referring again to FIG. 2, scene ICD 212 may be configured to capture images of a task space, such as surgical field 106 (FIG. 1), and computing device 202 can include any suitable image processing electronics and be programmed or otherwise configured to process images received from scene ICD 212. In particular, incision recognition application 226 is configured to analyze images received from scene ICD 212 to identify an incision, determine optimum lighting device settings for illuminating the incision, and automatically control lighting device 100 according to the determined settings. Using computer vision algorithms and techniques, incision recognition application 226 can recognize an incision. In some examples, system 200 may include a plurality of scene ICDs 212. In such instances, incision recognition application 226 can be configured to analyze the different views of the image capture devices separately or together (e.g., as a composite image) to determine one or more incision characteristics such as an incision size, shape, and depth.

In an example embodiment, computing device 202 receives images of surgical field 106 from scene ICD 212. Once received, incision recognition application 226 can be executed to process the images. In one example, incision recognition application 226 can incorporate computer vision algorithms and techniques to process the images to detect or otherwise determine if an incision is present and the characteristics of the incision. In some examples, incision recognition application 226 may utilize a training set of images to learn incisions. The set of images, in some embodiments, includes previous images of incisions. The set of images can be created from the perspective of a surgeon looking down on an incision. Incision recognition application 226 can learn various shapes of pixel groups that correspond to incisions, and then analyze the received images to determine if any group of pixels corresponds to a known incision (e.g., object classification using segmentation and machine learning).

In another example, a dotted line or other surface indicia may be drawn around a perimeter of a desired area of illumination. For example, in the example shown in FIGS. 6A-C, a dotted line is indicated at outer perimeters 606, 612, and 618. Incision recognition application 226 can be programmed to identify dotted lines or other surface indicia in surgical field 106 to determine a size and shape of the incision, which can be used to determine an optimum beam size and shape for illuminating the incision. Incision recognition application 226 can also be programmed to determine a depth of an incision by analyzing images captured by scene ICD 212 and adjust one or more of intensity and focal length of light, for example, increase intensity and/or focal length for deeper incisions and decrease intensity and/or focal length for shallower incisions.

Figure 7:
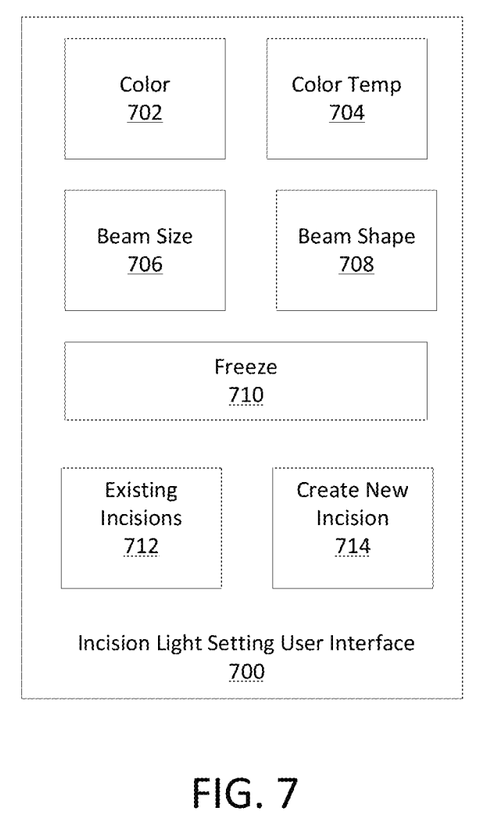
FIG. 7 illustrates an incision light setting user interface.

FIG. 7 illustrates an example embodiment of an incision light setting user interface (UI) 700 that may be communicatively coupled to computing device 202 and/or lighting device 100, e.g., via network 240 (FIG. 2), or through a direct wired or wireless connection, for controlling one or more settings of lighting system 200. In the illustrated example, incision light setting UI 700 may include color 702, color temperature 704, beam size 706, and beam shape 708 control elements that allow a user to manually adjust the color, color temperature, beam size, and beam shape, respectively, of light output by lighting device 100. Incision light setting UI 700 may also include a freeze button 710 for locking a current combination of settings selected by a user to prevent inadvertent further adjustment. Incision light setting UI 700 may also include an existing incision control feature 712 for selecting a previously saved combination of lighting device settings associated with a particular incision type, and a create new incision control feature 714 for saving a new combination of lighting device settings for a type of incision. Incision light setting UI 700 may can be used by a surgeon to customize the settings of lighting device 100 to his or her specific preferences by adjusting one or more of light color, color temperature, beam size and beam shape for a particular procedure. The surgeon can also save a combination of settings using the create new incision control feature 714 for future use, and can then access those saved settings at a later time via the existing incisions control feature 712.

Eye Position Sensor Calibration Procedure

Figure 8:
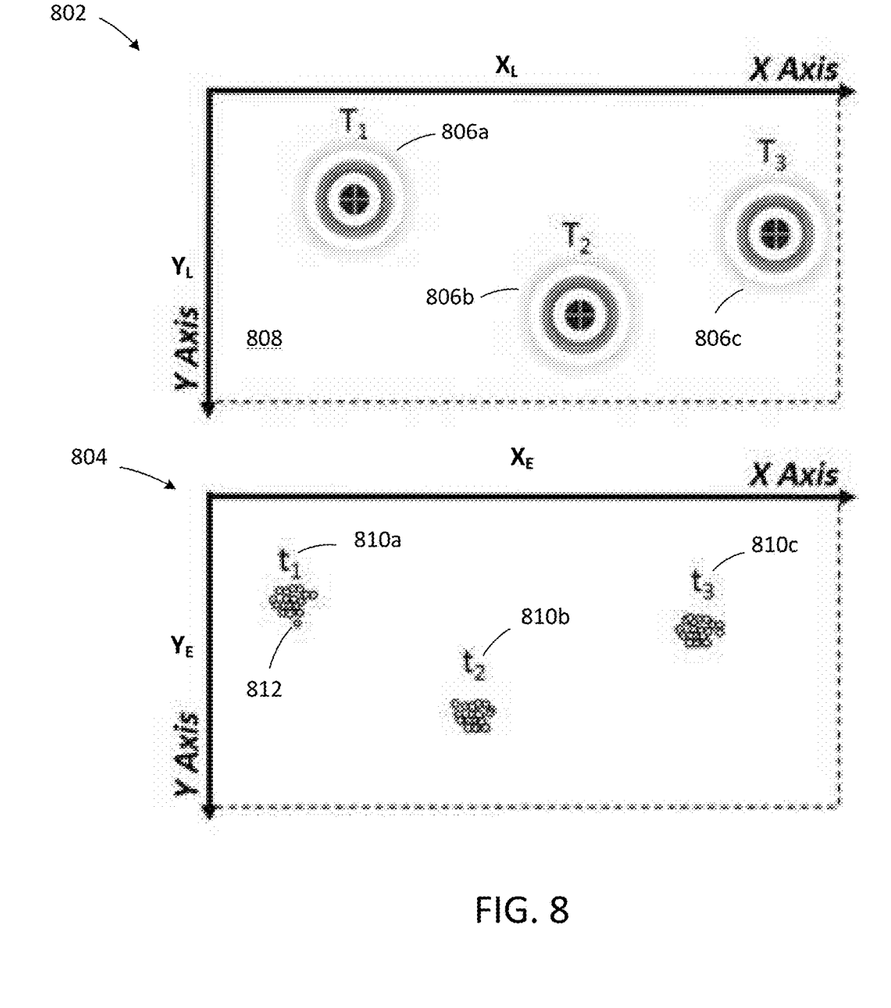
FIG. 8 illustrates a lighting device coordinate system and an eye position sensor coordinate system in connection with performing a calibration procedure for a lighting device with eye tracking and spatial beam control.
Figure 9:
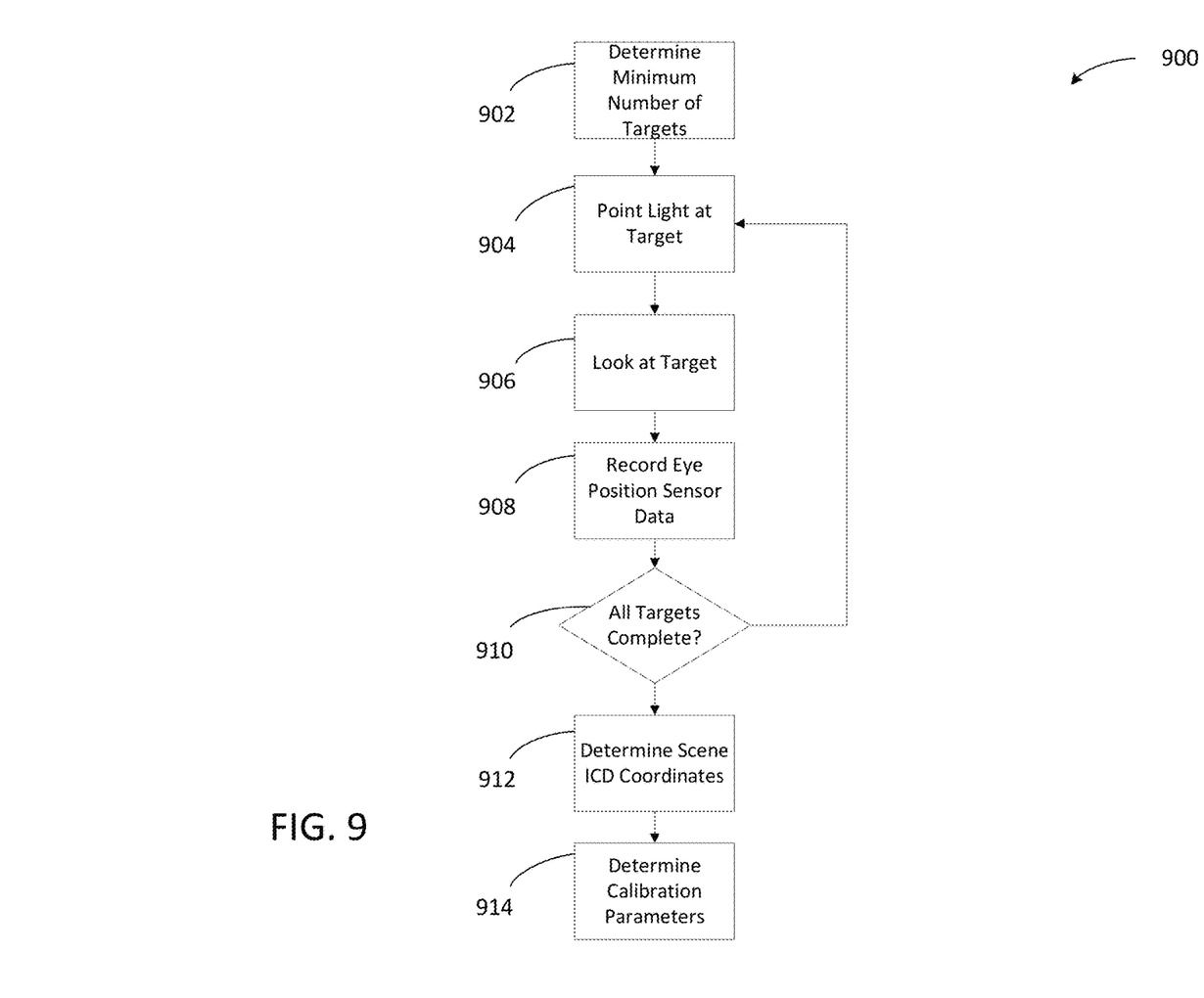
FIG. 9 illustrates a process for determining calibration parameters for calibrating an eye position sensor.

FIGS. 8 and 9 illustrate aspects of one embodiment of a calibration procedure for calibrating eye position sensor 210 with spatial control of the light beam generated by light source 204. Calibration application 231 (FIG. 2) may be programmed to perform one or more aspects of the illustrated calibration procedure and store the calculated calibration parameters in calibration database 234. FIG. 8 illustrates a lighting device coordinate system 802 with coordinates $x_L$, $y_L$ and an eye position sensor coordinate system 804 with coordinates $x_E$, $y_E$. A calibration procedure can be performed to correlate the two coordinate systems 802, 804 so that a point $x_E$, $y_E$ in the eye position sensor coordinate system 804 associated with a position of a user's eyes can be translated to a point $x_L$ in the lighting device coordinate system 802. Once the mapping between the two coordinate systems 802, 804 is obtained, a position of the beam of light generated by the lighting device can be located on substantially the same point the user is looking.

In the example illustrated in FIG. 8, lighting device is oriented and configured to sequentially direct a beam of light at, for example, a wall 808, at a plurality of different locations, the corresponding spots of illumination on the wall resulting in a plurality of targets 806a, 806b, 806c on a the wall 808. Eye position sensor 210 is operably arranged to monitor a position of a user's eyes, for example, by placing the eye position sensor on the user's face, and the user is instructed to look at targets 806. After a finite period of time, e.g., 3-5 seconds, the lighting device moves the location of the beam of light to a different one of the calibration locations, thereby forming the next target 806 on the wall, and the user is instructed to look at the target. FIG. 8 also illustrates data sets 810a, 810b, and 810c of eye position data generated by eye position sensor 210. Each small circle 812 (only one labeled) in each data set 810 represents a different eye position measurement generated by the eye position sensor and eye tracking application 228.

After acquiring eye position data 810, the calibration procedure may include estimating the most likely pairs of eye position sensor data $(x_{E1},y_{E1})$, $(x_{E2},y_{E2})$, $(x_{E3},y_{E3})$ from the data sets 810a, 810b, and 810c associated with targets $T_1$ (806a), $T_2$ (806b), and $T_3$ (806c), respectively. In one example, the most likely pairs can be determined using a weighted average of the prime candidates, acquired by filtering the outliers from the datasets 810.

A two-dimensional linear approximation can be used to correlate the lighting device coordinate system 802 and the eye position sensor coordinate system 804 as follows:

$$x_L = \alpha_1 x_E + \beta_1 u_E + c_1 \qquad \text{Eq. (1)}$$

$$y_L = \alpha_2 x_E + \beta_2 y_E + c_2 \qquad \text{Eq. (2)}$$

in which $\alpha 1$, $\alpha 2$, $\beta 1$, $\beta 2$, are calibration parameters contributing to the rotation of eye position sensor coordinate system 804 and c1 and c2 are parameters that account for translation of the eye position sensor coordinate system. The calibration parameters transform $x_E$, $y_E$, the 2D coordinates of the gaze position in the sensor coordinate system 804, to coordinates $x_L$, $y_L$ in lighting device coordinate system 802. In one example, linear approximation requires a one-to-one correspondence between an instance of $x_E$, $y_E$ and a corresponding respective output $x_L$, $y_L$. To obtain this correspondence, variability in the eye position sensor data in the allotted time of gazing at a target can be accounted for in a variety of ways. For example, eye position sensor 210 generates pairs of gaze coordinates (e.g., each circle 812) and a calibration procedure may include selecting a prime candidate $x_E$, $y_E$ for each target 806a, 806b and 806c. In the illustrated example, there are six unknowns ($\alpha 1$, $\alpha 2$, $\beta 1$, $\beta 2$, c1, and c2), at least three targets 806 may be used to obtain a solution for the six unknown calibration parameters.

In one example, a process of identifying prime candidates in the eye position sensor data sets 810 for each target, e.g., $(x_{E1},y_{E1})$, $(x_{E2},y_{E2})(x_{E3},y_{E3})$, is done by minimum mean square estimation. For each target, the prime candidate is selected by calculating a centroid from the corresponding gaze dataset 810 and selecting the data-point 812 that minimizes the mean square error from the centroid. In one example, at least one additional target 806 (e.g., a fourth target (not illustrated)) allows the calculation of any calibration error and may be used for rectification. In some examples, typical errors may range from about 1 to 50 pixels of scene ICD 212/506. In the event of a larger error, calibration application 231 can be programmed to recalibrate. In one example, recalibration arises when the user has not focused on one or more of the target locations in the allotted time. In another example, projecting the target light on a wall 808 parallel to the user can allow for the elimination of calibration parameters $\alpha 2$ and $\beta 1$, which would further simplify the calibration process.

FIG. 9 illustrates one example process 900 for determining calibration parameters for calibrating an eye position sensor, such as eye position sensor 210, with a lighting device with spatial beam control, such as lighting device 100. Calibration application 231 (FIG. 2) may be programmed to perform one or more aspects of process 900 and store the calculated calibration parameters in calibration database 234. In block 902, a minimum number of targets such as targets 806 (FIG. 8) for calibration procedure 900 are determined. As noted above, if the two-dimensional linear approximation described in equations (1) and (2) are used, then a sufficient number of data points for calculating the six calibration parameters of equations (1) and (2) are required. In block 904, the lighting device can be pointed at a first one of the targets and at block 906, the user can also look at the target. At block 908, eye position sensor data can be recorded and at block 910, blocks 904 through 908 can be repeated until all targets are complete, and then at block 912, the most likely pairs of eye position sensor data associated with each target can be determined. And at block 914, a mapping of coordinate systems can be applied to determine calibration parameters to translate future eye position coordinates generated by the eye position sensor to coordinates in the lighting device coordinate system. In the example provided herein, the two dimensional linear approximation includes calibration parameters that account for translation and rotation of the eye position sensor coordinate system as well as a constant to account for errors was used. In other examples, other correlations, such as correlations that incorporate non-linear equations, three dimensions, and additional error constants, may be used.

Any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
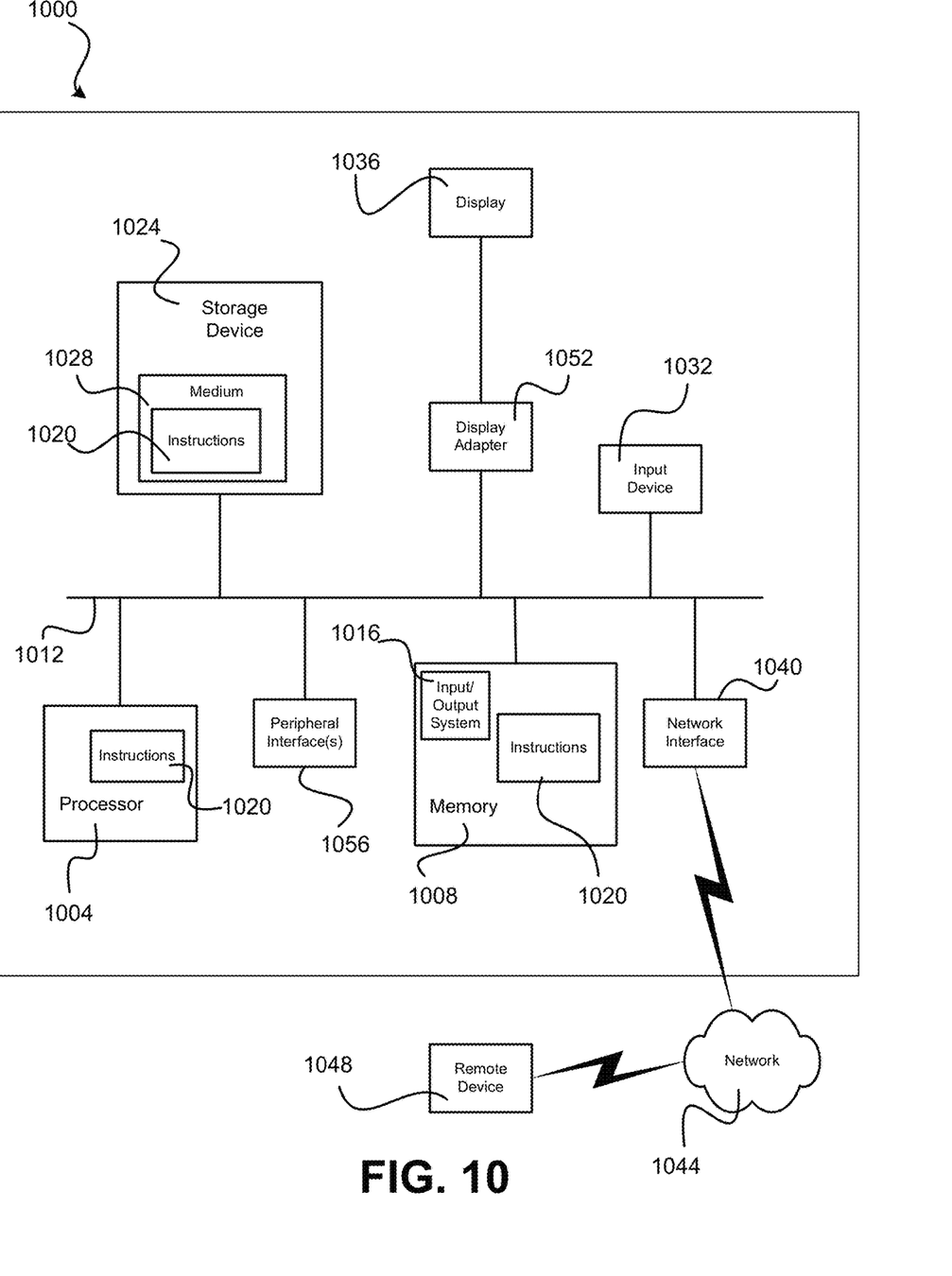
FIG. 10 shows a diagrammatic representation of one embodiment of a computing device that may be used for implementing lighting control methods of the present disclosure.

FIG. 10 shows a diagrammatic representation of one embodiment of a computing device in the form of a computer system 1000 within which a set of instructions for causing a control system, such as lighting system 200 of FIG. 2, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

Example embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A method of controlling a lighting device, comprising:
   receiving, at a processor, position sensor data, the position sensor data representing a position of at least one of a user's head and a user's eyes;
   determining, by the processor, whether the user is looking at a task area based on the position sensor data; and
   controlling, by the processor, an intensity of light emitted by the lighting device or turning the light on or off in response to determining whether the user is looking at the task area, wherein the lighting device is dimmed or turned off when the user is not looking at the task area and the lighting device is brightened or turned on to illuminate the task area when the user is looking at the task area.

2. The method of claim 1, wherein:
   the position sensor data is head position sensor data indicating a position of a user's head; and
   determining whether the user is looking at the task area comprises:
   calculating, by the processor, an angle of the user's head from the head position sensor data; and
   determining, by the processor, whether the calculated angle is within a first range of angles associated with the user looking at the task area.

3. The method of claim 1, wherein:
   the position sensor data is eye position sensor data indicating a position of a user's eyes; and
   determining whether the user is looking at the task area comprises:
   determining, by the processor, whether the eye position sensor data is within a first range of positions associated with the user looking at the task area.

4. The method of claim 3, wherein the first range of positions are associated with the user looking through loupes.

5. The method of claim 3, further comprising:
   determining, by the processor, a location where the user is looking based on the eye position sensor data; and
   controlling, by the processor, a location of a beam of light emitted by the lighting device to be substantially coincident with the location where the user is looking.

6. The method of claim 3, wherein the eye position sensor data is collected by an eye position sensor, and the method further comprises:
   pointing the lighting device at a first one of a plurality of targets;
   recording sensor data from the eye position sensor while a user is looking at the first one of the plurality of targets; and
   determining a set of calibrating parameters for translating a coordinate of the sensor data to a lighting device coordinate.

7. The method of claim 6, wherein the set of calibration parameters are parameters of a two-dimensional linear approximation.

8. The method of claim 6, wherein the set of calibration parameters represent a translation and a rotation of a coordinate system of the eye position sensor to a coordinate system of the lighting device.

9. A lighting system, comprising:
a lighting device;
a position sensor; and
a processor coupled to the lighting device and position sensor configured to:
   receive position sensor data from the position sensor, the position sensor data representing a position of at least one of a user's head and a user's eyes;
   determine whether the user is looking at a task area based on the position sensor data; and
   control an intensity of light emitted by the lighting device or turn the light on or off in response to determining whether the user is looking at the task area, wherein the lighting device is dimmed or turned off when the user is not looking at the task area and the lighting device is brightened or turned on to illuminate the task area when the user is looking at the task area.

10. The system of claim 9, wherein:
the position sensor is a head position sensor;
the position sensor data indicates a position of a user's head; and
the processor is further configured to:
   calculate an angle of the user's head from the position sensor data; and
   determine whether the calculated angle is within a first range of angles associated with the user looking at the task area.

11. The system of claim 9, wherein:
the position sensor is an eye position sensor;
the position sensor data indicates a position of a user's eyes; and
the processor is further configured to determine whether the position sensor data is within a first range of positions associated with the user looking at the task area.

12. The system of claim 11, wherein the first range of positions are associated with the user looking through loupes.

13. The system of claim 11, wherein the processor is further configured to:
   determine a location where the user is looking based on the position sensor data; and
   control a location of a beam of light emitted by the lighting device to be substantially coincident with the location where the user is looking.

14. The system of claim 11, wherein the processor is further configured to:
   point the lighting device at a first one of a plurality of targets;
   record sensor data from the eye position sensor while a user is looking at the first one of the plurality of targets; and
   determine a set of calibrating parameters for translating a coordinate of the sensor data to a lighting device coordinate.

15. The system of claim 14, wherein the set of calibration parameters are parameters of a two-dimensional linear approximation.

16. The system of claim 14, wherein the set of calibration parameters represent a translation and a rotation of a coordinate system of the eye position sensor to a coordinate system of the lighting device.

* * * * *